United States Patent
Caballero Catoira

(10) Patent No.: US 8,654,986 B2
(45) Date of Patent: Feb. 18, 2014

(54) SYSTEM FOR REMOTELY OBTAINING AUDIOMETRIC MEASUREMENTS AND ADJUSTING HEARING AIDS VIA THE INTERNET

(76) Inventor: Jose Benito Caballero Catoira, Coruna (ES)

(*) Notice: Subject to any disclaimer, the term of this patent is extended or adjusted under 35 U.S.C. 154(b) by 534 days.

(21) Appl. No.: 12/734,346

(22) PCT Filed: Oct. 24, 2008

(86) PCT No.: PCT/ES2008/070196
§ 371 (c)(1),
(2), (4) Date: Jun. 7, 2010

(87) PCT Pub. No.: WO2009/053517
PCT Pub. Date: Apr. 30, 2009

(65) Prior Publication Data
US 2010/0305469 A1 Dec. 2, 2010

(30) Foreign Application Priority Data
Oct. 25, 2007 (ES) .................................. 200702916

(51) Int. Cl.
*H04R 29/00* (2006.01)
(52) U.S. Cl.
USPC ........................................... 381/60; 600/559

(58) Field of Classification Search
USPC ............................................ 600/559; 381/60
See application file for complete search history.

(56) References Cited

U.S. PATENT DOCUMENTS

| | | | |
|---|---|---|---|
| 4,489,610 A * | 12/1984 | Slavin | 73/585 |
| 6,379,314 B1 * | 4/2002 | Horn | 600/559 |
| 2005/0192515 A1 * | 9/2005 | Givens et al. | 600/559 |

OTHER PUBLICATIONS

WIPO, International Search Report for PCT/ES2008/070196, Jan. 2009.

* cited by examiner

Primary Examiner — Max Hindenburg
Assistant Examiner — Renee Danega
(74) Attorney, Agent, or Firm — Eamonn Trainor

(57) ABSTRACT

System and method for remotely obtaining audiometric measurements and adjusting hearing aids via the Internet, using telematic means such as video conferencing and e-mail to establish a remote connection between the patient who may be at home, in a medical center or in a pharmacy and a hearing aid specialist at an audiometry laboratory or clinic, whereby the specialist remotely provides the patient with instructions for carrying out an audiometry test and, depending on the results, subsequently transmits adjustment signals via the Internet to the patient's hearing aid which is connected to a computer to which the patient has access.

7 Claims, No Drawings

SYSTEM FOR REMOTELY OBTAINING AUDIOMETRIC MEASUREMENTS AND ADJUSTING HEARING AIDS VIA THE INTERNET

OBJECT OF THE INVENTION

The present invention consists of a system for obtaining a method of adapting hearing aids which permits audiometry tests to be performed and the hearing aid to be adjusted by means of organizing the communication via the Internet between a hearing aid specialist and the patient.

BACKGROUND OF THE INVENTION

Currently, the diagnosis and adaptation of hearing aids are done in a hearing aid specialist's office, in which the patient has to be present.

The hearing aid specialist normally follows a protocol such as the one below, to find out the level of hearing:
- In a soundproof room such as that disclosed in Spanish patent ES2049167, of the same inventor as the present invention, a series of pure tones is emitted in different frequencies, beginning at 1000 Hz and at 40 Dbs, lowering the Dbs in 5 Db increments until the patient says that they cannot hear them, or raising them in 5 Db increments in the event that they cannot hear the 40 Dbs. This protocol is repeated in all of the frequencies to be examined.
- Once this data has been collected, the hearing aid specialist draws up a graph which represents the minimum hearing threshold by frequency, which serves as a starting point to amplify the hearing aid.
- The amplification of the hearing aid is done through an interface, applying previously stipulated methods provided by each hearing aid manufacturer, and which, depending on the minimum hearing threshold obtained, automatically adapts the hearing aid.

There are numerous patented inventions related to the application of computing resources for audiometry, and which in some cases allow the audiometry tests to be performed, but not the remote adjustment of the hearing aid.

For example, Spanish patent ES21880409 discloses a digital audiometer which uses the computer connection to send the signal to a compatible interface in its outlet, producing an excitation of the ear phones or bone vibrator to determine the hearing threshold of a patient.

Spanish patent ES2115552 discloses a controlled computing method to diagnose the state of people's hearing and is intended to provide a monitoring of the auditory function of the workers which, due to noises in the workplace, could lead to some hearing loss. A similar application is disclosed in United States patent US2002/0076056 which allows, via the Internet, hearing tests to be carried out for the employees of a company and the historical record of each worker to be saved in a data base which is accessible from the same computer program from which the hearing tests were performed.

Patent WO00/64350 discloses a method performed by computer to easily diagnose the auditory state of a patient, just as do patents US2001/0051775 and WO01/26272, which highlight the possibility of making an assessment or diagnosis of the hearing capacity via the Internet without the patient having to attend the clinic to see the doctor.

There even exist patents which disclose inventions to produce and store hearing profiles of a client while at the same time creating personalized audio data bases to the clients' profiles, such as patent WO01/24576.

U.S. Pat. No. 7,181,297 discloses an invention relating to the distribution of personalized audio products (songs, videos, etc.) according to the clients' listening profile.

DESCRIPTION OF THE INVENTION

There are statistics which state that currently 9% of the population is hearing impaired. This group tends to increase due to the high level of ambient noise and to the gradual aging of the population, reaching a percentage of 80% in the 80 and older age range of the population.

The present invention consists of a method of adapting hearing aids which allow hearing tests and also the subsequent adjustment of the hearing aid to be performed through telematic means such as video conferencing, the Internet, etc., remotely connecting the patient, whether it is from their home or from a medical care center or pharmacy, with a hearing aid specialist situated in their clinic or audiometric laboratory.

The patient and the hearing aid specialist are in contact through video conferencing and the Internet, via which the hearing protocol is carried out and, once the minimum hearing threshold has been established, the level of amplification of the hearing aid is adapted by sending the data over the Internet.

But this system is also applicable for checking the corrective ability of the hearing aid with the assistance of an available anechoic chamber, whether in the patient's home or, more often, in the clinical centers or pharmacies where the patient connects with the hearing aid specialist. The patient sends the result of the hearing aid corrective ability verification to the hearing aid specialist via the Internet, and the hearing aid specialist would correct these results in their medical office, using the same systems as they currently use, but instead of having to do so in the presence of the patient, they will do so from a distance.

The hearing aid adaption system via the Internet or modem tries to draw the patient and the hearing aid specialist closer together, and can even allow the purchase of hearing aids over the Internet, all of this being especially advantageous for many people who are elderly, ill, have limited mobility, or are in a physically delicate state. It can even be advantageous for people who do not have these physical problems but who live in low-density population areas or where geographic mobility is difficult during the entire year, or during part of the year.

PREFERRED EMBODIMENT OF THE INVENTION

A preferred embodiment of the invention, which shall be understood in a broad and non-limitative sense, is detailed below.

The system for remotely obtaining audiometric measurements and adjusting hearing aids via the Internet is made up of the following elements:
- A digital hearing aid with a built-in system which allows a wire or wireless connection to a computer.
- A personal computer situated in the patient's home or in a clinic or pharmacy close to the patient's residence.
- A computer program which adjusts the hearing aid via the Internet.
- A personal computer in the hearing aid specialist's clinic.
- A web camera in the hearing aid specialist's clinic connected to the hearing aid specialist's personal computer.
- A soundproof anechoic chamber or cabin (soundproof cabin being understood at a moment in which the background noise is less than 40 Dbs), situated in the patient's home or in a clinic or pharmacy close to the patient's residence.

A control device based in a central processing unit which governs the devices and computer programs between the patient and the equipment situated in the hearing aid specialist's office, and which are interconnected via the Internet.

A wireless or cable data transmission device which connects the various computer terminals.

The hearing aid specialist uses the web camera and the personal computer situated in their office to connect with the patient's computer via the Internet. The hearing aid specialist explains the entire audiometric measurement process to the patient through their web camera, so that the data and images are transmitted to the screen of the computer to which the patient is connected, and the patient shall closely take note of the hearing aid specialist's instructions, following the steps that are indicated. Specifically, the hearing aid specialist places a hearing aid in their ear, and invites the patient to do the same via the web camera so that they can correct the possible mistakes made by the patient during the audiometric procedure at all times.

The patient does not just receive visual messages on their computer screen, but also receives audible messages through the loudspeakers connected to their computer or through the hearing aid itself, further facilitating the communication with the hearing aid specialist.

Once the patient has placed their hearing aid, which is connected by a cable or wirelessly to their computer, in their ear, they proceed to the first tonal audiometry data collection test, which consists of sending a series of pure tones through the hearing aid specialist-patient connection, beginning with a frequency of 1000 Hz at an intensity of 40 Dbs, and asking the patient if they hear it. The patient, through their computer, will respond affirmatively or negatively. In the event of an affirmative reply, the intensity will be reduced by 5 Dbs and the question will be repeated, reducing the Dbs by 5 Db increments until the patient can no longer hear it. The reference point will be the last tone that they can still hear.

In the event that the patient cannot hear the first tone sent, the tone will be increased in 5 Db increments until they begin to hear it, the reference point in this case being the first tone that the patient hears.

All of the frequencies to be examined (500 Hz, 2000 Hz, 3000 Hz, etc.) are then tested in the same manner, thereby obtaining the minimum hearing threshold by frequencies, which will allow the discovery of where the amplification of the hearing aid needs to begin.

The adaptation of the hearing aid will be done by means of prescriptive methods established by the different hearing aid manufacturers to program their devices, and which take the minimum hearing threshold calculated as a reference point.

Additionally, the system also incorporates the possibility of carrying out a vocal hearing test, providing the patient with a series of standard digitalized and tested words, which has the advantage of not being subject to the hearing aid specialist's changes of voice when this is the person giving the tests. This test allows one to reliably find out the way the patient hears, even in noisy atmospheres which the series of tests can simulate.

Once the hearing aid specialist has all of the data obtained from the previously described procedures, they will send, via the Internet, a signal to the patient's hearing aid through the patient's computer to which the hearing aid is connected through an interface by using a suitably programmed computer program, so that these signals adjust the hearing aid to the patient's hearing loss.

The hearing aid specialist will be able to observe the patient's degree of satisfaction and correct the adaptation just as they would in the case of both of them being physically present in the same office.

Likewise, if during the normal use of the hearing aid, the user detects a problem, or if the hearing aid specialist wants to verify that the hearing aid works correctly after carrying out an audiometry test, they can check whether the state of the hearing aid is correct through the same protocol described previously to calculate the minimum hearing threshold, and analyze any error thereof. To do that, the patient would remotely connect to the hearing aid specialist through their computer or prepared terminal in a pharmacy, clinic, etc., to receive instructions to fix the adjustment problem.

The patient can check the state of their hearing aid in an anechoic chamber situated in their home or normally in a pharmacy or clinic near their residence, or wherever they are at each moment (on a trip, on vacation, etc.), and telematically send, if necessary, information to the hearing aid specialist with the measurement data in the anechoic chamber. The hearing aid specialist will proceed to send a new adjustment signal to the patient's hearing aid via the telematic network.

A data base can be set up in the hearing aid specialist's computer with the recorded data of each patient, which is greatly useful.

This system if efficient, versatile, fast, and completely programmable, so it is possible to include new audiometric and adaptation tests solely by modifying the programming of the computer program.

The invention claimed is:

1. A method for remotely obtaining audiometric measurements and adjusting hearing aids between a patient and a hearing aid specialist, comprising the following steps:
   a computer from said hearing aid specialist's medical office is connected to the patient's computer via a telematic network,
   a web camera from the hearing aid specialist sends data and images with instructions to the patient's computer screen,
   a series of incrementally increasing and decreasing sequences in pure tone intensity, for a specific number of frequencies, are sent from the hearing aid specialist's computer to the patient's computer, and which are reproduced through loud speakers connected to the patient's computer, or through a hearing aid connected to the patient's computer,
   the patient sends, at least, affirmative signals confirming that they can hear, from their computer to the hearing aid specialist's computer,
   the hearing aid specialist calculates a minimum hearing threshold of the patient for each one of the pure tone emission frequencies according to the affirmative signals confirming that they could hear them,
   the hearing aid specialist's computer sends, via the telematic network, an adjustment signal of the patient's hearing aid generated according to the patient's said minimum hearing thresholds and which are received in the patient's computer
   the hearing aid connected to the patient's computer is adjusted according to said adjustment signal.

2. A method for remotely obtaining audiometric measurements and adjusting hearing aids between a patient and a hearing aid specialist, according to the previous claim, additionally comprising the following steps:

the patient receives audio signals to check whether their hearing aid is correctly reprogrammed to their necessities by means of an anechoic chamber, the patient sends information through telematic means to the hearing aid specialist with the measurement data in the anechoic chamber, the hearing aid specialist sends a new signal to adjust the patient's hearing aid via the telematic network, the signal being calculated according to said measurement data in the anechoic chamber, the hearing aid being adjusted accurately.

3. A method for remotely obtaining audiometric measurements and adjusting hearing aids between a patient and a hearing aid specialist, according to claim 1, whereas the hearing aid specialist complements the audiometry by sending the patient a series of standard digitalized and tested words.

4. A method for remotely obtaining audiometric measurements and adjusting hearing aids between a patient and a hearing aid specialist, according to claim 2, whereas the hearing aid specialist complements the audiometry by sending the patient a series of standard digitalized and tested words.

5. A method for remotely obtaining audiometric measurements and adjusting hearing aids between a patient and a hearing aid specialist, according to claim 1, whereas the hearing aid specialist's computer registers the historical record of measurements and adjustments of the patient in a data base.

6. A method for remotely obtaining audiometric measurements and adjusting hearing aids between a patient and a hearing aid specialist, according to claim 2, whereas the hearing aid specialist's computer registers the historical record of measurements and adjustments of the patient in a data base.

7. A method for remotely obtaining audiometric measurements and adjusting hearing aids between a patient and a hearing aid specialist, according to claim 3, whereas the hearing aid specialist's computer registers the historical record of measurements and adjustments of the patient in a data base.

\* \* \* \* \*